（12）United States Patent
Kostrzewski

(10) Patent No.: US 8,807,139 B1
(45) Date of Patent: Aug. 19, 2014

(54) ORAL AIR DELIVERY SYSTEM FOR CPAP

(71) Applicant: Kris A. Kostrzewski, Sylvania, OH (US)

(72) Inventor: Kris A. Kostrzewski, Sylvania, OH (US)

( * ) Notice: Subject to any disclaimer, the term of this patent is extended or adjusted under 35 U.S.C. 154(b) by 98 days.

(21) Appl. No.: 13/624,027

(22) Filed: Sep. 21, 2012

(51) Int. Cl.
*A61C 5/14* (2006.01)

(52) U.S. Cl.
USPC ..................................... 128/862; 128/204.18

(58) Field of Classification Search
CPC .......... A61M 2015/002; A61M 15/00; A61M 2016/0036; A61M 16/0488; A61M 16/0666; A61M 16/06; A61M 2016/0661; A61M 2016/0493; A61M 16/0875; A61M 2016/1095; A61M 15/06; A61M 15/08; A61M 16/0495; A61M 16/0683; A61M 16/0816; A61M 16/1075; A61M 16/08; A61M 15/0065; A61M 2015/0003; A61M 2015/0043; A61M 2015/0048; A61M 2015/0051; A61M 2015/0055; A61M 2015/0068; A61B 5/087; A61B 10/0051; A61B 5/055; A61B 5/0813; A61B 5/411; A61B 5/097; A61H 2201/1697; A61H 31/02; A61H 9/0078; A61H 1/003; A62B 7/00; A62B 7/02; A62B 7/10; A61F 5/566; A61F 2005/563; A61F 5/00; A61J 7/0061; A24F 47/002; A24F 47/006; A41D 13/11

USPC .............. 128/204.18, 206.29, 848, 859–862; 433/6; 602/902
See application file for complete search history.

(56) References Cited

U.S. PATENT DOCUMENTS

| | | | |
|---|---|---|---|
| 4,813,933 A * | 3/1989 | Turner | 604/79 |
| 8,091,554 B2 * | 1/2012 | Jiang | 128/848 |
| 8,122,890 B2 * | 2/2012 | Vaska | 128/848 |
| 8,333,202 B2 * | 12/2012 | Lyons | 128/848 |
| 8,607,796 B2 * | 12/2013 | Thornton | 128/848 |
| 2006/0112962 A1 * | 6/2006 | Tebbutt et al. | 128/206.29 |
| 2008/0276938 A1 * | 11/2008 | Jeppesen et al. | 128/204.18 |
| 2009/0241969 A1 * | 10/2009 | Walker | 128/848 |

OTHER PUBLICATIONS

Beecroft, Jaime et al.; Oral Continuous Positive Airway Pressure for Sleep Apnea; Chest Dec. 2003; vol. 124; No. 6 2200-2208.
www.fphcare.com; Oracle Oral Mask; internet; as of Mar. 31, 2012.

* cited by examiner

*Primary Examiner* — Michael A. Brown

(57) ABSTRACT

A novel oral air delivery system for CPAP or similar machines featuring a mouthpiece adapted to be inserted in a user's mouth between his/her teeth and a tube connected to the mouthpiece via a swivel joint. The swivel joint allows rotation of the tube with respect to the mouthpiece. The tube of the system can be connected to existing CPAP or similar machines. Air is delivered from the CPAP or similar machine through the tube and through a hole in the mouthpiece to the user's mouth, throat, and lungs.

15 Claims, 11 Drawing Sheets

Top view

Bottom view

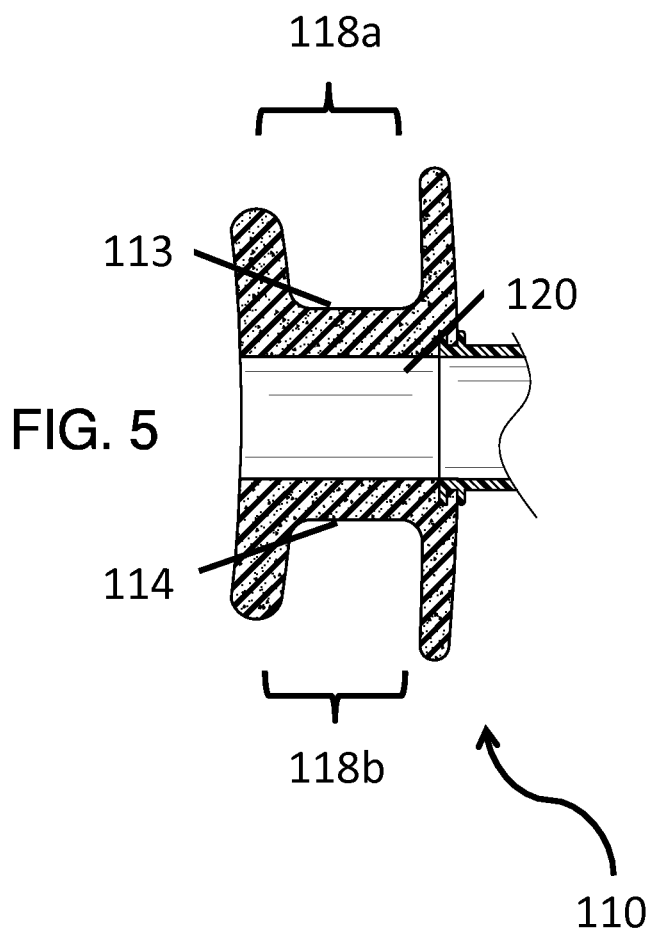

110

ORAL AIR DELIVERY SYSTEM FOR CPAP

BACKGROUND OF THE INVENTION

Continuous positive airway pressure (CPAP) is a commonly used treatment for sleep apnea. CPAP systems deliver, via a mask, air under pressure. The pressurized air makes passes through the obstructing tissues in the throat to the lungs. CPAP therapy may be nasal (e.g., through a mask covering a nose and forcing air through nostrils), oral (e.g., through a mask covering the mouth), or both (e.g., through a full face mask, forcing air through nostrils and mouth). CPAP machines typically feature a computer controlled airflow generator that generates an airstream at a constant pressure. An alternative to CPAP includes variable positive airway pressure (VPAP), also known as bislevel positive airway pressure (BiPAP). VPAP machines typically monitor the patients breathing and provide two different pressures, a higher pressure during inhalation and a lower pressure during exhalation.

The present invention features a novel oral air delivery system for CPAP machines or similar machines such as VPAP machines. The system of the present invention features a combination mouthpiece and tube piece. The system can be connected to existing CPAP machines or other appropriate machines such as VPAP machines. With the system of the present invention, CPAP machines can deliver air through the user's partially opened lips (e.g., the present invention doesn't require a face mask sealed to the user's face with straps, although the present invention may be used in combination with a face mask and/or a strap if desired).

Without wishing to limit the present invention to any theory or mechanism, it is believed that the system of the present invention is advantageous because the system may be beneficial for those individuals who are mouth breathers, the system may be more comfortable than a system requiring a sealed face mask, the system may allow for mandibular forward protrusion (e.g., opening of airway), and/or the system may encourage patient compliance.

SUMMARY

The present invention features an oral air delivery system for CPAP or similar machines. In some embodiments, the system comprises a mouthpiece and a tube. The mouthpiece is arc-shaped and has a top surface, a bottom surface, a first side edge, and a second side edge opposite the first side edge. The first side edge has a longer arc length than does the second side edge. The first side edge extends a first distance above the top surface of the mouthpiece, the second side edge extends a second distance above the top surface of the mouthpiece, the first side edge extends a third distance below the bottom surface of the mouthpiece, and the second side edge extends a fourth distance below the bottom surface of the mouthpiece.

A first gap exists between the portion of the first side edge raised above the top surface of the mouthpiece and the portion of the second side edge raised above the top surface of the mouthpiece. A second gap exists between the portion of the first side edge extending below the bottom surface of the mouthpiece and the portion of the second side edge extending below the bottom surface of the mouthpiece.

The first gap (118a) is adapted to sandwich teeth of a user's upper jaw, and the second gap (118b) is adapted to sandwich teeth of a user's lower jaw. The first gap (118a) and the second gap (118b) are aligned on the same plane so as to align the teeth (e.g., central incisors) of the upper jaw and the teeth (e.g., central incisors) of the lower jaw.

A hole is disposed mouthpiece about halfway between outer edges of the mouthpiece. The hole is situated below the top surface of the mouthpiece and above the bottom surface of the mouthpiece. In some embodiments, the hole is linear, e.g., the hole has a height smaller than its width. The hole allows passage of air from the first side edge to the second side edge of the mouthpiece The tube has a first end attached to a first end of the hole via a swivel joint. The swivel joint allows for rotation of the tube with respect to the mouthpiece. An adaptor component is disposed on a second end of the tube, the adaptor component engages a CPAP machine, wherein air can pass through the tube and through the hole and into a user's mouth, wherein air can pass from a user's mouth through the hole.

In some embodiments, the mouthpiece can be adjusted to fit a user's teeth. In some embodiments, the mouthpiece is constructed from a material that allows thermal molding of the mouthpiece to a user's teeth. In some embodiments, the tube can rotate 360 degrees about the mouthpiece via the swivel joint. In some embodiments, the tube is between about 10 to 16 inches in length as measured from the first end to the second end. In some embodiments, the tube has a diameter between about ⅜ inch and ¾ inch. In some embodiments, the mouthpiece comprises a plurality of holes situated below the top surface of the mouthpiece and above the bottom surface of the mouthpiece.

The present invention also features a method of providing continuous positive airway pressure (CPAP). In some embodiments, the method comprises providing an oral air delivery system of the present invention, engaging the tube with a standard continuous positive airway pressure (CPAP) machine and activating said CPAP machine; and repositioning a user's jaw by placing the mouthpiece in the user's mouth, wherein the teeth of the upper jaw are sandwiched by the first gap and the teeth of the lower jaw are sandwiched by the second gap. The alignment of the gaps aligns the teeth of the upper jaw and the teeth of the lower jaw.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 5 is a side cross sectional view of the mouthpiece of the system of the present invention.

DESCRIPTION OF PREFERRED EMBODIMENTS

Figure 1:
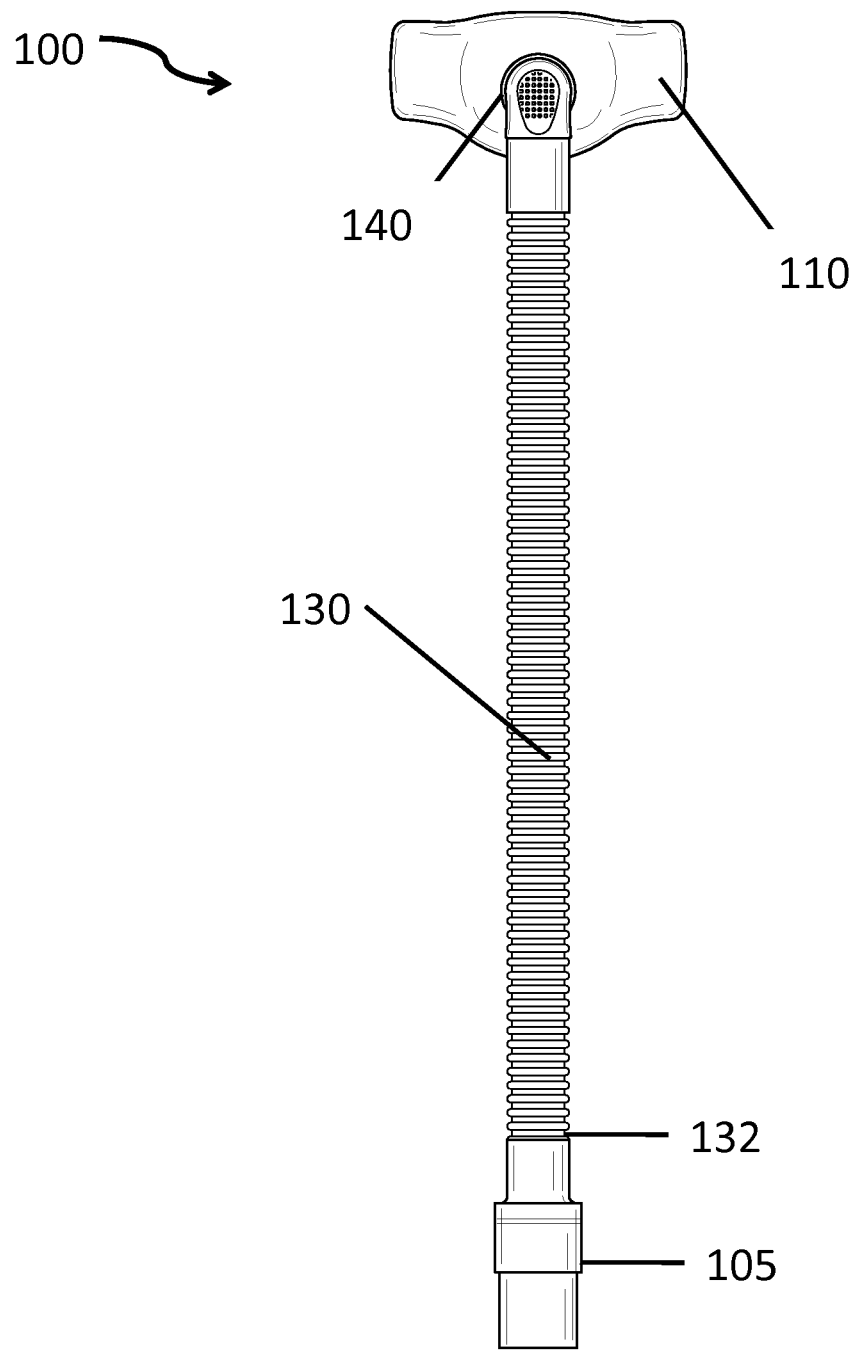
FIG. 1 is a front view of the system of the present invention.
Figure 2:
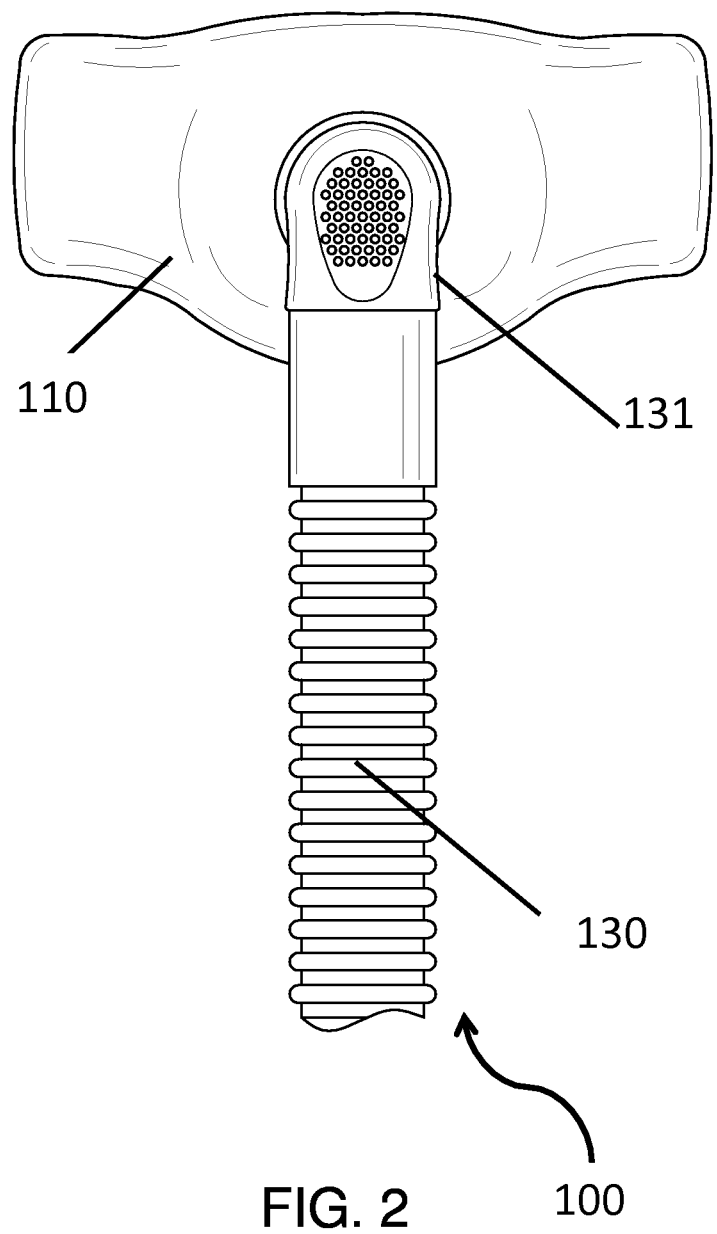
FIG. 2 is a front detailed view of the system of the present invention.
Figure 3:
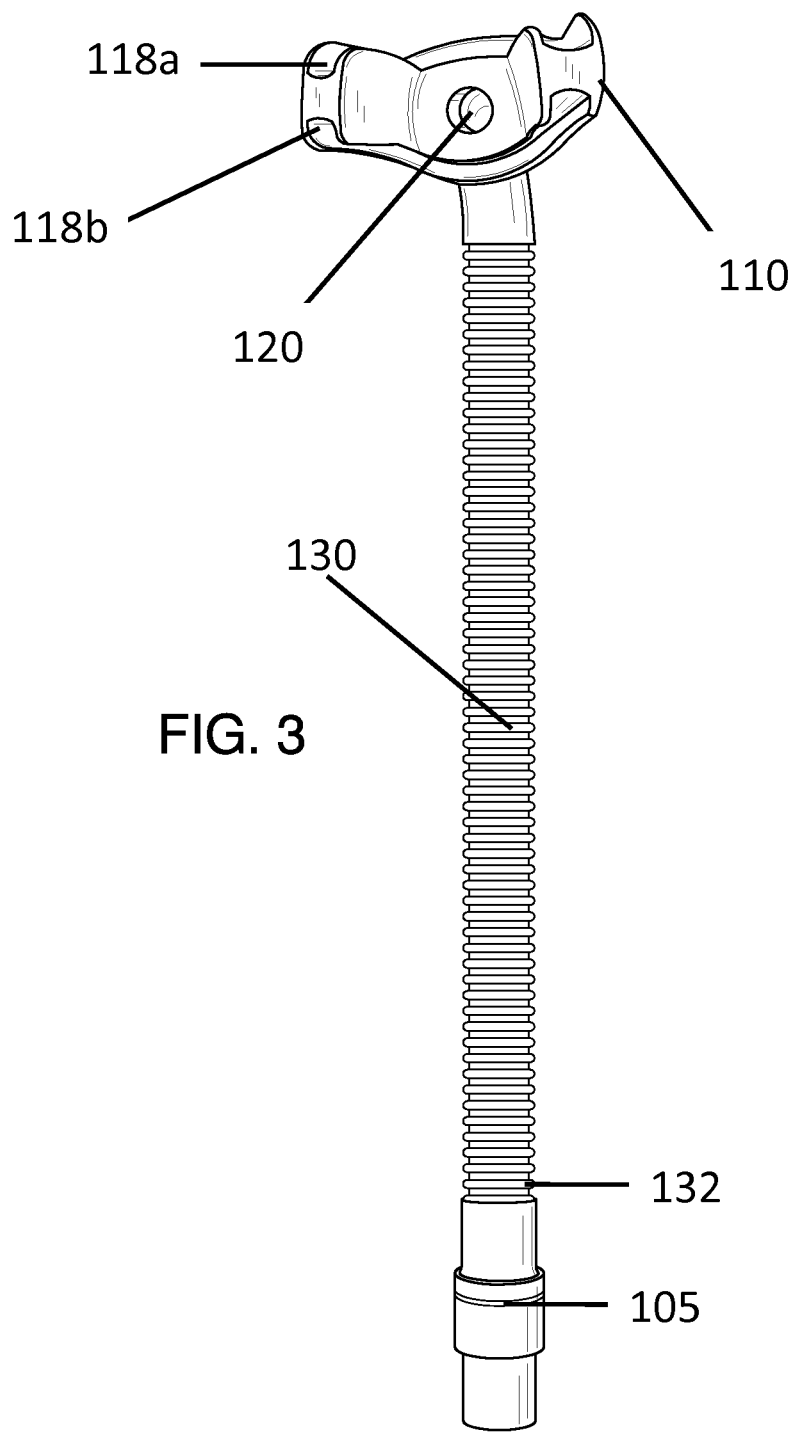
FIG. 3 is a back view of the system of the present invention.

Referring now to FIG. 1-6, the present invention features a novel oral air delivery system (100) for CPAP machines (or similar machines, such as VPAP machines).

The system (100) comprises a mouthpiece (110) and a tube (130). The mouthpiece (110) is arc-shaped, e.g., the mouthpiece (110) is in the shape of a standard adult's set of top teeth. The mouthpiece (110) has a top surface (113), a bottom surface (114), a first side edge (111), and a second side edge (112) opposite the first side edge (111). The first side edge (111) has a longer arc length than does the second side edge (112). The first side edge (111) extends a first distance above the top surface (113) of the mouthpiece (110). The second side edge extends a second distance above the top surface (113) of the mouthpiece (110). The first side edge (111) extends a third distance below the bottom surface (114) of the mouthpiece (110). The second side edge extends a fourth distance below the bottom surface (114) of the mouthpiece (110). The first distance, second distance, third distance, and fourth distance may be the same or different.

A first gap (118a) exists between the portion of the first side edge (111) raised above the top surface (113) of the mouthpiece (110) and the portion of the second side edge (112) raised above the top surface (113) of the mouthpiece (110). The first gap 118a accommodates a user's top teeth. When the mouthpiece (110) engages the user's top teeth, the portion of the first side edge (111) that is raised above the top surface (113) of the mouthpiece (110) covers a portion of the front of the user's top teeth.

A second gap (118b) exists between the portion of the first side edge (111) extending below the bottom surface (114) of the mouthpiece (110) and the portion of the second side edge (112) extending below the bottom surface (114) of the mouthpiece (110). The second gap 118b accommodates a user's bottom teeth. When the mouthpiece (110) engages the user's bottom teeth, the portion of the first side edge (111) extending below the bottom surface (114) of the mouthpiece (110) covers a portion of the front of the user's bottom teeth.

The first gap (118a) is adapted to sandwich teeth of a user's upper jaw, and the second gap (118b) is adapted to sandwich teeth of a user's lower jaw. In some embodiments, the first gap (118a) and the second gap (118b) are aligned on the same plane. This provides mandibular repositioning (assuming the user has a normal bite) such that the central incisors of the upper and lower jaws are aligned on the same plane. For example, the central incisors of the upper and lower jaws are within 0 mm to 1 mm of each other (e.g., along the vertical plane), within 0 mm to 2 mm of each other (e.g., along the vertical plane), within 0 mm to 3 mm of each other (e.g., along the vertical plane), within 0 mm to 4 mm of each other (e.g., along the vertical plane), etc. For example, in some embodiments, the alignment of the gaps (118) forces the lower jaw slightly forward.

Figure 4:
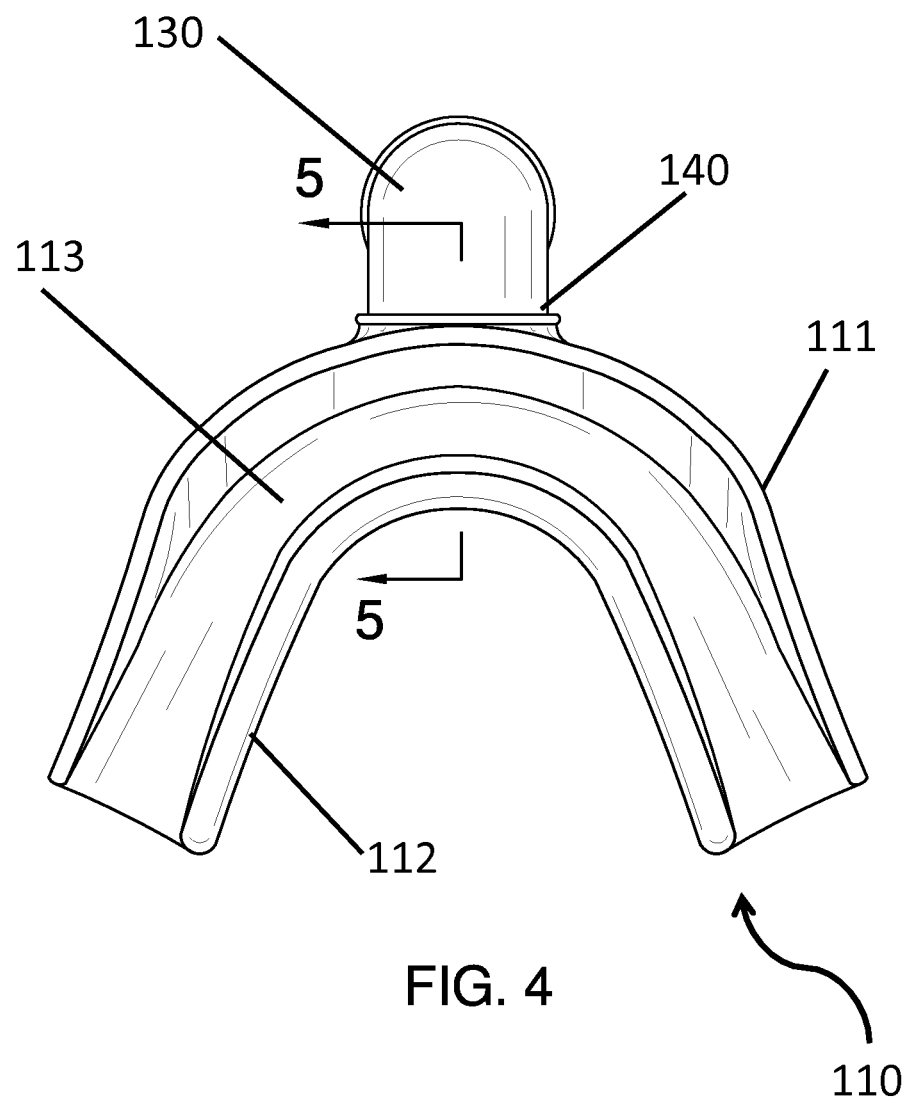
FIG. 4 is a detailed perspective view of the mouthpiece of the system of the present invention.
Figure 4A:
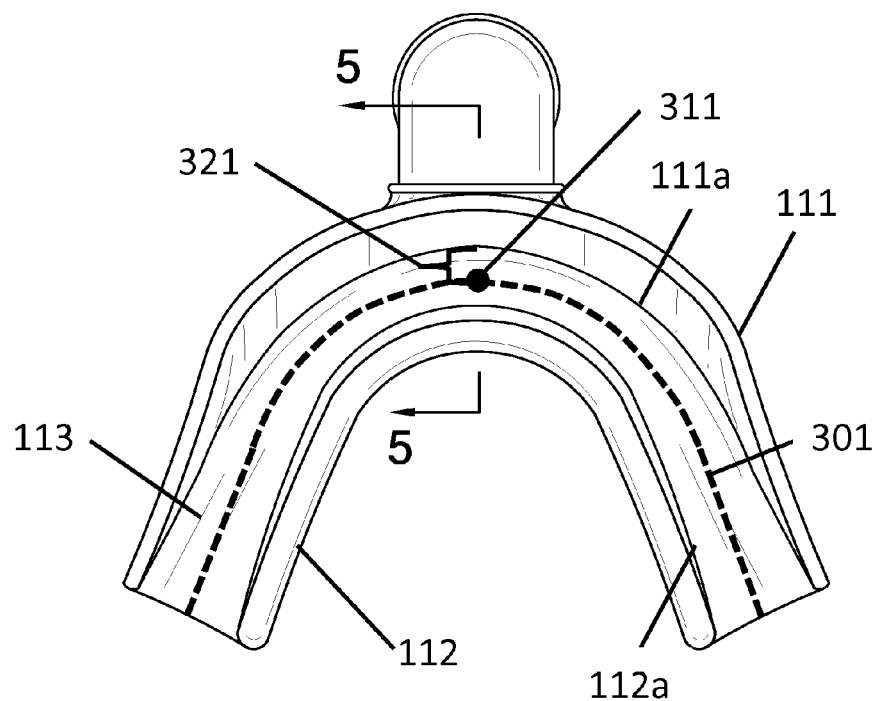
FIG. 4A is a top view of the mouthpiece of the system of the present invention.
Figure 4B:
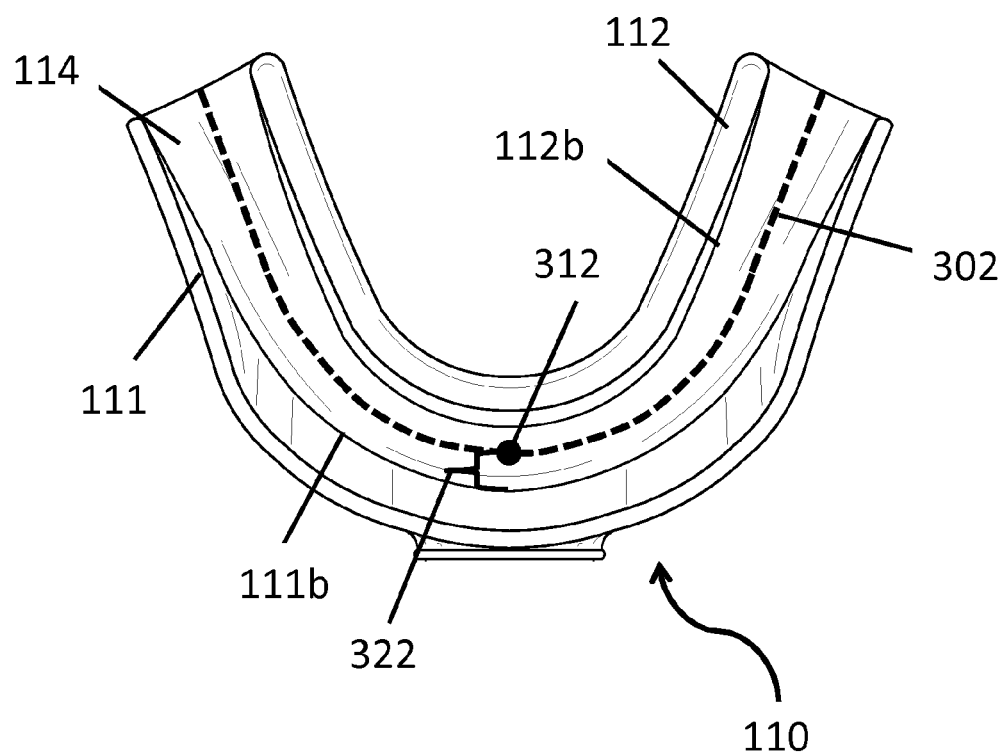
FIG. 4B is a bottom view of the mouthpiece of the system of the present invention.

As shown in FIG. 4A, the mouthpiece (110) comprises a first line (301) that extends along the top surface (113) of the mouthpiece (110), e.g., along the entire arc length of the top surface (113) of the mouthpiece (110). The first line (301) is positioned halfway between the first intersection (111a) and the second intersection (112a) of the mouthpiece (110), the first intersection (111a) referring to the intersection of the first side edge (111) and the top surface (113) of the mouthpiece (110) and the second intersection (112a) referring to the intersection of the second side edge (112) and the top surface (113) of the mouthpiece (110). A first point (311) lies on the first line (301) and is positioned at the vertex of the first line (301).

As shown in FIG. B, the mouthpiece (110) comprises a second line (302) that extends along the bottom surface (114) of the mouthpiece (110), e.g., along the entire arc length of the bottom surface (114) of the mouthpiece (110). The second line (302) is positioned halfway between the third intersection (111b) and the fourth intersection (112b) of the mouthpiece (110), the third intersection (111b) referring to the intersection of the first side edge (111) and the bottom surface (114) of the mouthpiece (110) and the fourth intersection (112b) referring to the intersection of the second side edge (112) and the bottom surface (114) of the mouthpiece (110). A second point (312) lies on the second line (302) and is positioned at the vertex of the second line (302).

As shown in FIG. 4A, FIG. 4B, FIG. 5A, and FIG. 5B, in some embodiments, the first distance (321) between the first point (311) of the first line (301) and the first intersection (111a) of the mouthpiece (110) is greater than or equal to the second distance (322) between the second point (312) of the second line (302) and the third intersection (111b) of the mouthpiece (110). In some embodiments, the third distance (323) between the first point (311) of the first line (301) and the second intersection (112a) of the mouthpiece (110) is less than or equal to the fourth distance (324) between the second point (312) of the second line (302) and the fourth intersection (112b) of the mouthpiece (110). These configurations may help ensure that the central incisors of the user's lower jaw are moved (e.g., forwardly, for a standard individual's dental bite) so as to be aligned with the central incisors of the upper jaw. In some embodiments, the teeth of the user's lower jaw are slightly forward as compared to the teeth of the upper jaw. For example, in some embodiments, the mouthpiece (110) repositions a user's jaw such that the central incisors of the upper jaw and the central incisors of the lower jaw are aligned.

In some embodiments, the first distance (321) is equal to the second distance (322). In some embodiments, the first distance (321) is between about 0.1 mm and 0.5 mm greater than the second distance (322). In some embodiments, the first distance (321) is between about 0.5 mm and 1 mm greater than the second distance (322). In some embodiments, the first distance (321) is between about 1 mm and 2 mm greater than the second distance (322). In some embodiments, the first distance (321) is between about 2 mm and 4 mm greater than the second distance (322). In some embodiments, the first distance (321) is more than about 4 mm greater than the second distance (322).

In some embodiments, the third distance 323) is equal to the fourth distance (324). In some embodiments, the third distance (323) is between about 0.1 mm and 0.5 mm less than the fourth distance (324). In some embodiments, the third distance (323) is between about 0.5 mm and 1 mm less than the fourth distance (324). In some embodiments, the third distance (323) is between about 1 mm and 2 mm less than the fourth distance (324). In some embodiments, the third distance (323) is between about 2 mm and 4 mm less than the fourth distance (324). In some embodiments, the third distance (323) is more than about 4 mm less than the fourth distance (324).

Figure 5A:
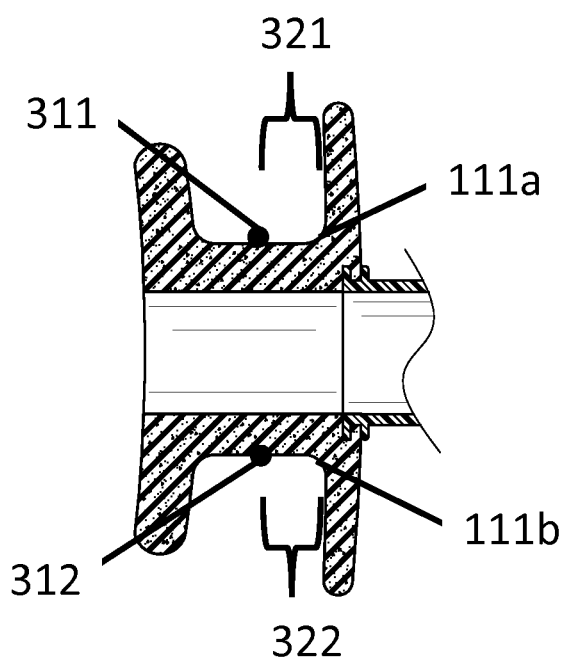
FIG. 5A is a side cross sectional view of the mouthpiece of the system of the pr; invention.
Figure 5B:
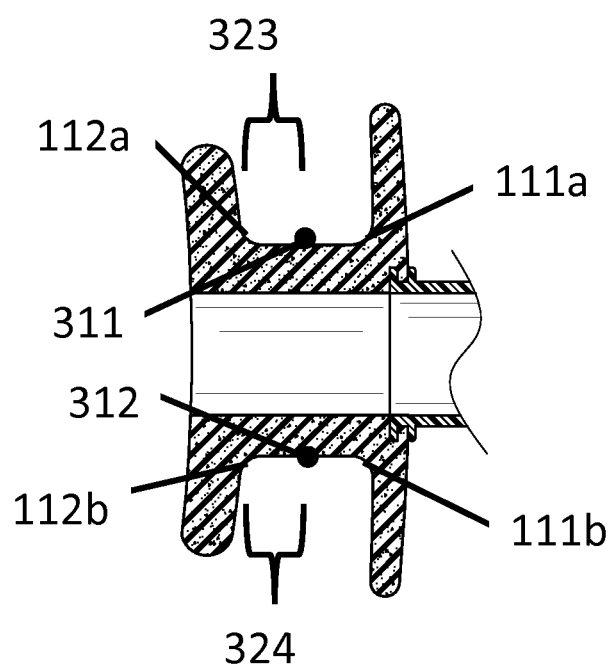
FIG. 5B is a side cross sectional view of the mouthpiece of the system of the present invention.
Figure 5C:
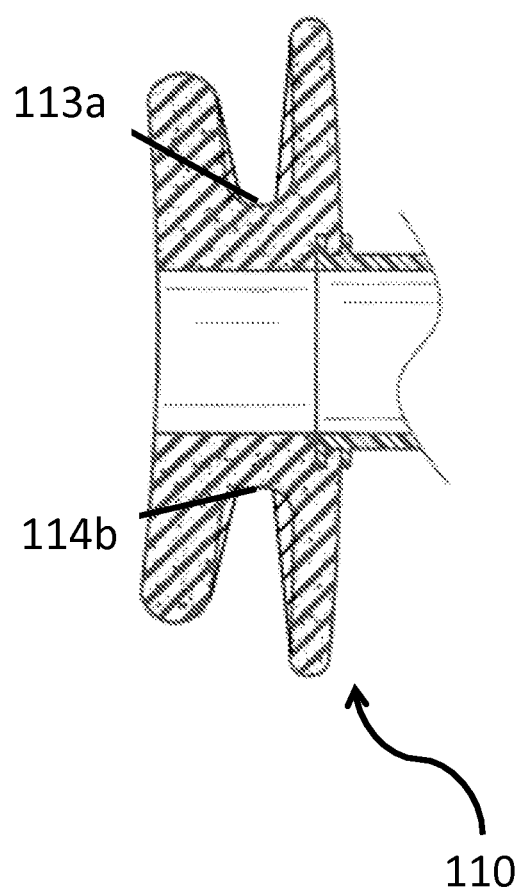
FIG. 5C is a side cross sectional view of an alternative embodiment of the mouthpiece of the system of the present invention.

As shown in FIG. 5C, the gaps (118) are not necessarily rectangular in shape (as viewed from the side cross section). In some embodiments, the first side edge (111) and the second side edge (112) are angled inwardly or are curved inwardly, forming a top deepest region (113a) in the top surface (113) of the mouthpiece (110) and a bottom deepest region (114b) in the bottom surface of the mouthpiece (110). In some embodiments, the top deepest region (113a) and the bottom deepest region (114) are aligned, (e.g., are within 0 mm to 1 mm of each other, are within 0 mm to 2 mm of each other, are within 0 mm to 3 mm of each other, are within 0 mm to 4 mm of each other, etc.) so as to allow the central incisors of the upper jaw and the central incisors of the lower jaw to align.

In some embodiments, the mouthpiece (110) is constructed such that the portion of the top surface (113) of the mouthpiece (110) that comes into contact with the tip of the central incisors of the upper jaw aligns with the portion of the bottom surface (114) of the mouthpiece (110) that comes into contact with the tip of the central incisors of the lower jaw.

Without wishing to limit the present invention to any theory or mechanism, the gaps (118) of the mouthpiece (110) of the system (100) of the present invention are continuous, e.g., the gaps (118) form an arc around the entire length of the mouthpiece (110) as compared to snorkel or scuba mouthpieces, which only provide small gaps (118) on the outer edges of the mouthpiece (110).

The mouthpiece (110) may be constructed from a variety of materials. For example, in some embodiments, the mouthpiece (110) is constructed from a material comprising plastic or any other appropriate material for a mouth guard or similar device. In some embodiments, the mouthpiece (110) is constructed to fit a user's teeth, e.g., the mouthpiece (110) is custom made. In some embodiments, the mouthpiece (110) is constructed to be able to fit the user's teeth, e.g., via subjecting the mouthpiece (110) to heat (e.g., boiling water) and molding the mouthpiece (110) to the user's teeth. For example, the mouthpiece (110) may be constructed from a thermal-fit material. Such thermal molding methods and thermal fit materials are used for mouth guards for sports and the like. The mouthpiece (110) may be adjustable via other means, e.g., via cutting or trimming, bending, etc.

A hole (120) is disposed mouthpiece (110), e.g., about halfway between the outer edges of the mouthpiece (110). The hole (120) is situated below the top surface (113) of the mouthpiece (110) and above the bottom surface (114) of the mouthpiece (110). The hole (120) is adapted to allow passage of air in and out of the mouthpiece (110) (e.g., from the first side edge (111) to the second side edge (112) of the mouthpiece (110)). For example, air from the tube (130) passes through the mouthpiece (110) in between the user's top teeth and bottom teeth and into the user's mouth and throat (and lungs). Similarly, air exits the mouth via the hole (120).

Figure 6A:
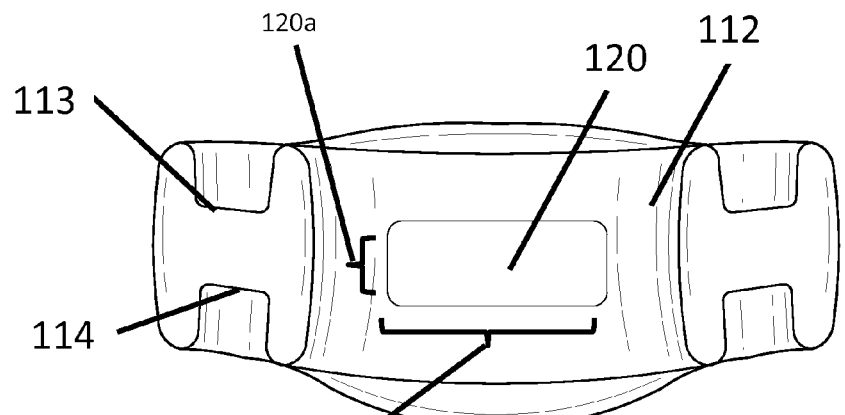
FIG. 6A is a front view of the mouthpiece of the system of the present invention.
Figure 6B:
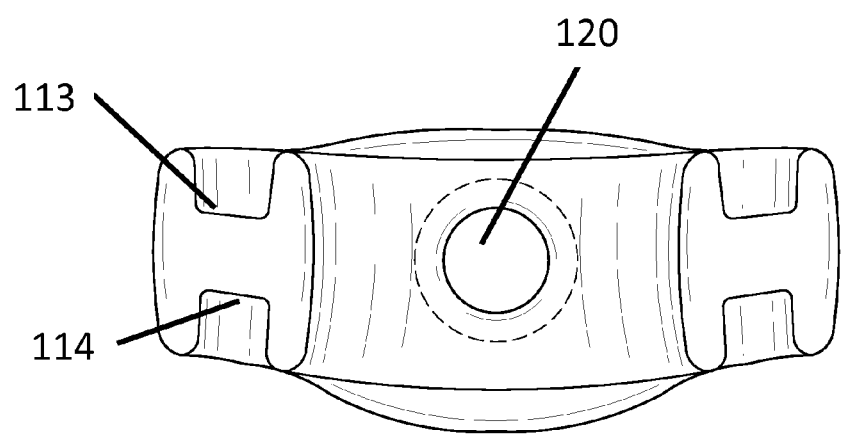
FIG. 6B is a front view of the mouthpiece of the system of the present invention.

In some embodiments, the hole (120) is linear (see FIG. 6A). For example, in some embodiments, the hole (120) has a height (120a) smaller than its width (120b). The linear-shaped hole may help provide for a smaller mouthpiece (110), e.g., as measured from the top surface (113) to the bottom surface (114), which may allow a user to keep his/her mouth in a more closed position as compared to a mouthpiece with a larger size or distance between the top surface (113) and bottom surface (114). In some embodiments, the mouthpiece (110) comprises a plurality of holes (120). In some embodiments, the hole (120) is circular (see FIG. 66), oval, or any other appropriate shape.

In some embodiments, the mouthpiece is between about 0.25 to 0.5 inches in height as measured from the top surface (113) to the bottom surface (114). In some embodiments, the mouthpiece is between about 0.5 to 1 inch in height as measured from the top surface (113) to the bottom surface (114).

In some embodiments, the mouthpiece is between about 0.5 to 1.5 inches in height as measured from the top surface (113) to the bottom surface (114).

The hole (120) has a first end and a second end. The first end is positioned in the first side edge (111) of the mouthpiece (110) and the second end is positioned in the second side edge (112) of the mouthpiece (110). The first end (131) of the tube (130) is connected to the hole (120), e.g., the first end of the hole (120). In some embodiments, the tube (130) is removably attached to the hole (120). In some embodiments, the tube (130) is fixedly attached to the hole (120).

In some embodiments, the tube (130) is attached to the hole (120) via a swivel joint (140). The swivel joint (140) allows for rotation of the tube (130) with respect to the mouthpiece (110). For example, in some embodiments, the tube (130) can rotate 360 degrees about the mouthpiece via the swivel joint (140).

The second end (132) of the tube (130) is adapted to engage a CPAP machine (or similar machine, e.g., VPAP machine). For example, an adaptor component (105) is disposed on the second end (132) of the tube (130), wherein the adaptor component (105) engages the CPAP or similar machine. Such adaptors for engaging CPAP or similar machines are well known to one of ordinary skill in the art.

The tube (130) may be constructed from a variety of materials and in a variety of sizes. For example, in some embodiments, the tube (130) is between about 8 to 12 inches in length as measured from the first end (131) to the second end (132). In some embodiments, the tube (130) is between about 10 to 16 inches (e.g., 14 inches) in length as measured from the first end (131) to the second end (132). The tube (130) is not limited to the aforementioned lengths. For example, in some embodiments, the tube (130) is less than about 8 inches in length. In some embodiments, the tube (130) is more than about 16 inches in length. In some embodiments, the diameter of the tube (130), e.g., the outside diameter, is between about ⅜ inch to ¾ inch (e.g., ⅝ inch). The diameter of the tube (130), e.g., the outer diameter, is not limited to the aforementioned dimensions. For example, in some embodiments, the diameter of the tube (130), e.g., the outside diameter, is less than about ⅜ inch. In some embodiments, the diameter of the tube (130), e.g., the outside diameter, is more than about ¾ inch.

Without wishing to limit the present invention to any theory or mechanism, it is believe that the present invention is advantageous because the system (190) provides mandibular positioning such that the teeth of the lower jaw are pushed (e.g., pushed forward) such that the teeth of the lower jaw are aligned with the teeth of the upper jaw.

As used herein, the term "about" refers to plus or minus 10% of the referenced number. For example, an embodiment wherein the tube (130) is about 10 inches in length includes a tube (130) that is between 9 and 11 inches in length.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and

What is claimed is:

1. An oral air delivery system (100) comprising:
   (a) a mouthpiece (110), the mouthpiece (110) is arc-shaped and has a top surface (113), a bottom surface (114), a first side edge (111), and a second side edge (112) opposite the first side edge (111), the first side edge (111) has a longer arc length than does the second side edge (112), the first side edge (111) extends a first distance above the top surface (113) of the mouthpiece (110), the second side edge extends a second distance above the top surface (113) of the mouthpiece (110), the first side edge (111) extends a third distance below the bottom surface (114) of the mouthpiece (110), the second side edge extends a fourth distance below the bottom surface (114) of the mouthpiece (110), wherein a first gap (118a) exists between the portion of the first side edge (111) raised above the top surface (113) of the mouthpiece (110) and the portion of the second side edge (112) raised above the top surface (113) of the mouthpiece (110) and a second gap (118b) exists between the portion of the first side edge (111) extending below the bottom surface (114) of the mouthpiece (110) and the portion of the second side edge (112) extending below the bottom surface (114) of the mouthpiece (110), the first gap (118a) is adapted to sandwich teeth of a user's upper jaw and the second gap (118b) is adapted to sandwich teeth of a user's lower jaw, the first gap (118a) and the second gap (118b) are aligned on a same plane so as to align central incisors of the upper jaw and central incisors of the lower jaw, wherein a hole (120) is disposed in the mouthpiece (110) about halfway between outer edges of the mouthpiece (110), the hole (120) is situated below the top surface (113) of the mouthpiece (110) and above the bottom surface (114) of the mouthpiece (110), the hole (120) is linear having a height (120a) smaller than a width (120b), the hole (120) allows passage of air from the first side edge (111) to the second side edge (112) of the mouthpiece; and
   (b) a hollow tube (130), a first end (131) of the tube (130) is attached to a first end of the hole (120) via a swivel joint (140), the swivel joint (140) allows for rotation of the tube (130) with respect to the mouthpiece (110), an adaptor component (105) is disposed on a second end (132) of the tube (130), the adaptor component (105) engages a CPAP machine, wherein air can pass through the tube (130) and through the hole (120) and into a user's mouth, wherein air can pass from a user's mouth through the hole (120).

2. The system (100) of claim 1, wherein the mouthpiece (110) comprises:
   (a) a first line (301) that extends along the top surface (113) of the mouthpiece (110), the first line (301) is positioned halfway between a first intersection (111a) and a second intersection (112a) of the mouthpiece (110), the first intersection (111a) being an intersection of the first side edge (111) and the top surface (113) of the mouthpiece (110) and the second intersection (112a) being an intersection of the second side edge (112) and the top surface (113) of the mouthpiece (110), a first point (311) lies on the first line (301) and is positioned at a vertex of the first line (301); and
   (b) a second line (302) that extends along the bottom surface (114) of the mouthpiece (110), the second line (302) is positioned halfway between a third intersection (111b) and a fourth intersection (112b) of the mouthpiece (110), the third intersection (111b) being an intersection of the first side edge (111) and the bottom surface (114) of the mouthpiece (110) and the fourth intersection (112b) being an intersection of the second side edge (112) and the bottom surface (114) of the mouthpiece (110), a second point (312) lies on the second line (302) and is positioned at a vertex of the second line (302);
   wherein a first distance (321) between the first point (311) of the first line (301) and the first intersection (111a) of the mouthpiece (110) is greater than or equal to a second distance (322) between the second point (312) of the second line (302) and the third intersection (111b) of the mouthpiece (110).

3. The system (100) of claim 1, wherein the mouthpiece (110) comprises:
   (a) a first line (301) that extends along the top surface (113) of the mouthpiece (110), the first line (301) is positioned halfway between a first intersection (111a) and a second intersection (112a) of the mouthpiece (110), the first intersection (111a) being an intersection of the first side edge (111) and the top surface (113) of the mouthpiece (110) and the second intersection (112a) being an intersection of the second side edge (112) and the top surface (113) of the mouthpiece (110), a first point (311) lies on the first line (301) and is positioned at a vertex of the first line (301); and
   (b) a second line (302) that extends along the bottom surface (114) of the mouthpiece (110), the second line (302) is positioned halfway between a third intersection (111b) and a fourth intersection (112b) of the mouthpiece (110), the third intersection (111b) being an intersection of the first side edge (111) and the bottom surface (114) of the mouthpiece (110) and the fourth intersection (112b) being an intersection of the second side edge (112) and the bottom surface (114) of the mouthpiece (110), a second point (312) lies on the second line (302) and is positioned at a vertex of the second line (302);
   wherein a third distance (323) between the first point (311) of the first line (301) and the second intersection (112a) of the mouthpiece (110) is less than or equal to a fourth distance (324) between the second point (312) of the second line (302) and the fourth intersection (112b) of the mouthpiece (110).

4. The system (100) of claim 1, wherein a top deepest region (113a) in the top surface (113) of the mouthpiece (110) and a bottom deepest region (114b) in the bottom surface of the mouthpiece (110) are aligned as to allow central incisors of the upper jaw and central incisors of the lower jaw to align.

5. The system (100) of claim 4, wherein the top deepest region (113a) in the top surface (113) of the mouthpiece (110) and the bottom deepest region (114b) in the bottom surface of the mouthpiece (110) are within 0 mm to 3 mm of each other.

6. The system (100) of claim 1, wherein a portion of the top surface (113) of the mouthpiece (110) that comes into contact with tips of central incisors of the upper jaw aligns with a portion of the bottom surface (114) of the mouthpiece (110) that comes into contact with tips of central incisors of the lower jaw.

7. The system (100) of claim 1, wherein the mouthpiece (110) is constructed from a material that allows thermal molding of the mouthpiece (110) to a user's teeth.

8. The system (100) of claim 1, wherein the tube (130) can rotate 360 degrees about the mouthpiece via the swivel joint (140).

9. The system (100) of claim 1, wherein the tube (130) is between about 10 to 16 inches in length as measured from the first end (131) to the second end (132).

10. The system (100) of claim 1, wherein the tube (130) has a diameter between about ⅜ inch to ¾ inch.

11. The system (100) of claim 1, wherein the mouthpiece (110) comprises a plurality of holes (120) situated below the top surface (113) of the mouthpiece (110) and above the bottom surface (114) of the mouthpiece (110).

12. A method of providing continuous positive airway pressure (CPAP), said method comprising:
(a) providing an oral air delivery system (100) comprising
(i) a mouthpiece (110), the mouthpiece (110) is arc-shaped and has a top surface (113), a bottom surface (114), a first side edge (111), and a second side edge (112) opposite the first side edge (111), the first side edge (111) has a longer arc length than does the second side edge (112), the first side edge (111) extends a first distance above the top surface (113) of the mouthpiece (110), the second side edge extends a second distance above the top surface (113) of the mouthpiece (110), the first side edge (111) extends a third distance below the bottom surface (114) of the mouthpiece (110), the second side edge extends a fourth distance below the bottom surface (114) of the mouthpiece (110), wherein a first gap (118a) exists between the portion of the first side edge (111) raised above the top surface (113) of the mouthpiece (110) and the portion of the second side edge (112) raised above the top surface (113) of the mouthpiece (110) and a second gap (118b) exists between the portion of the first side edge (111) extending below the bottom surface (114) of the mouthpiece (110) and the portion of the second side edge (112) extending below the bottom surface (114) of the mouthpiece (110), the first gap (118a) is adapted to sandwich teeth of a user's upper jaw and the second gap (118b) is adapted to sandwich teeth of a user's lower jaw, the first gap (118a) and the second gap (118b) are aligned on a same plane so as to align central incisors of the upper jaw and central incisors of the lower jaw, wherein a hole (120) is disposed in the mouthpiece (110) about halfway between outer edges of the mouthpiece (110), the hole (120) is situated below the top surface (113) of the mouthpiece (110) and above the bottom surface (114) of the mouthpiece (110), the hole (120) is linear having a height (120a) smaller than a width (120b), the hole (120) allows passage of air from the first side edge (111) to the second side edge (112) of the mouthpiece; and (ii) a hollow tube (130), a first end (131) of the tube (130) is attached to a first end of the hole (120) via a swivel joint (140), the swivel joint (140) allows for rotation of the tube (130) with respect to the mouthpiece (110), an adaptor component (105) is disposed on a second end (132) of the tube (130), the adaptor component (105) engages a CPAP machine, wherein air can pass through the tube (130) and through the hole (120) and into a user's mouth, wherein air can pass from a user's mouth through the hole (120);
(b) engaging the tube (130) with a standard continuous positive airway pressure (CPAP) machine and activating said CPAP machine; and
(c) repositioning a user's jaw by placing the mouthpiece (110) in the user's mouth wherein the teeth of the upper jaw are sandwiched by the first gap (118a) and the teeth of the lower jaw are sandwiched by the second gap (118b), the alignment of the gaps (118) aligns central incisors of the upper jaw and central incisors of the lower jaw.

13. The system (100) of claim 12, wherein the tube (130) can rotate 360 degrees about the mouthpiece via the swivel joint (140).

14. An oral air delivery system (100) comprising:
(a) a mouthpiece (110), the mouthpiece (110) is arc-shaped and has a top surface (113), a bottom surface (114), a first side edge (111), and a second side edge (112) opposite the first side edge (111), the first side edge (111) has a longer arc length than does the second side edge (112), the first side edge (111) extends a first distance above the top surface (113) of the mouthpiece (110), the second side edge extends a second distance above the top surface (113) of the mouthpiece (110), the first side edge (111) extends a third distance below the bottom surface (114) of the mouthpiece (110), the second side edge extends a fourth distance below the bottom surface (114) of the mouthpiece (110), wherein a first gap (118a) exists between the portion of the first side edge (111) raised above the top surface (113) of the mouthpiece (110) and the portion of the second side edge (112) raised above the top surface (113) of the mouthpiece (110) and a second gap (118b) exists between the portion of the first side edge (111) extending below the bottom surface (114) of the mouthpiece (110) and the portion of the second side edge (112) extending below the bottom surface (114) of the mouthpiece (110), the first gap (118a) is adapted to sandwich teeth of a user's upper jaw and the second gap (118b) is adapted to sandwich teeth of a user's lower jaw, the first gap (118a) and the second gap (118b) are aligned on a same plane so as to align central incisors of the upper jaw and central incisors of the lower jaw, wherein a hole (120) is disposed in the mouthpiece (110) about halfway between outer edges of the mouthpiece (110), the hole (120) is situated below the top surface (113) of the mouthpiece (110) and above the bottom surface (114) of the mouthpiece (110), the hole (120) is linear having a height (120a) smaller than a width (120b), the hole (120) allows passage of air from the first side edge (111) to the second side edge (112) of the mouthpiece;
(b) teeth of a user's upper jaw sandwiched by the first gap (118a) and teeth of a user's lower jaw sandwiched by the second gap (118b), the mouthpiece is configured such that central incisors of the upper jaw are aligned with central incisors of the lower jaw; and
(b) a hollow tube (130), a first end (131) of the tube (130) is attached to a first end of the hole (120) via a swivel joint (140), the swivel joint (140) allows for rotation of the tube (130) with respect to the mouthpiece (110), an adaptor component (105) is disposed on a second end (132) of the tube (130), the adaptor component (105) engages a CPAP machine, wherein air can pass through the tube (130) and through the hole (120) and into a user's mouth, wherein air can pass from a user's mouth through the hole (120).

15. The system (100) of claim 14, wherein the tube (130) can rotate 360 degrees about the mouthpiece via the swivel joint (140).

* * * * *